United States Patent [19]

Baker et al.

[11] Patent Number: 5,385,720
[45] Date of Patent: * Jan. 31, 1995

[54] COMPOSITIONS OF IODOBENZOIC ACID DERIVATIVES AND CELLULOSE DERIVATIVES FOR VISUALIZATION OF THE GASTROINTESTINAL TRACT

[75] Inventors: Edward J. Baker, Northumberland, England; Robert W. Lee, Gilbertsville, Pa.; Carl R. Illig, Phoenixville, Pa.; Brent D. Douty, Coatesville, Pa.; John L. Toner, Downingtown, Pa.

[73] Assignee: Sterling Winthrop Inc., Malvern, Pa.

[*] Notice: The portion of the term of this patent subsequent to May 17, 2011 has been disclaimed.

[21] Appl. No.: 216,988

[22] Filed: Mar. 23, 1994

Related U.S. Application Data

[63] Continuation-in-part of Ser. No. 29,756, Mar. 11, 1993, Pat. No. 5,312,616.

[51] Int. Cl.$^6$ .................. A61K 49/04; A61K 31/715; A61K 31/235
[52] U.S. Cl. ........................... 424/5; 514/57; 514/533; 514/543; 514/544; 514/717
[58] Field of Search ............ 424/5; 514/57, 717, 514/533, 543, 544

[56] References Cited

U.S. PATENT DOCUMENTS

| | | | |
|---|---|---|---|
| 2,572,828 | 10/1951 | Archer | 260/612 |
| 2,622,100 | 12/1952 | Newbery et al. | 260/31.4 |
| 3,317,569 | 5/1967 | Larsen et al. | 260/347.4 |
| 3,360,436 | 12/1967 | Felder et al. | 167/95 |
| 3,361,700 | 1/1968 | Archer et al. | 260/473 |
| 3,558,691 | 1/1971 | Pyne | 260/473 |
| 4,044,048 | 8/1977 | Felder et al. | 260/475 P |

FOREIGN PATENT DOCUMENTS 1259565 9/1989 Canada .

*Primary Examiner*—Gary E. Hollinden
*Attorney, Agent, or Firm*—Arthur Rosenstein; Imre (Jim) Balogh

[57] ABSTRACT

Disclosed are x-ray contrast compositions for oral or retrograde examination of the gastrointestinal tract comprising an x-ray producing agent of the formula or a pharmaceutically acceptable salt thereof

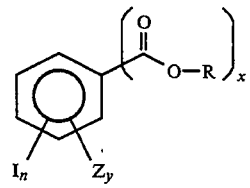

wherein Z is H, halo, $C_1$–$C_{20}$ alkyl, cycloalkyl, lower alkoxy, cyano, where the alkyl and cycloalkyl groups can be substituted with halogen or halo-lower-alkyl groups;

R is $C_1$–$C_{25}$ alkyl, cycloalkyl, or halo-lower-alkyl, each of which may be optionally substituted with halo, fluoro-lower-alkyl, aryl, lower-alkoxy, hydroxy, carboxy, lower-alkoxy carbonyl or lower-alkoxy-carbonyloxy;

$(CR_1R_2)_p$— $(CR_3=CR_4)_mQ$, or $(CR_1R_2)_p$—C≡C—Q;

$R_1$, $R_2$, $R_3$ and $R_4$ are independently lower-alkyl, optionally substituted with halo;

x is 1—3
y is 1—4;
n is 1—5;
m is 1—15;
p is 1—10; and

Q is H, lower-alkyl, lower-alkenyl, lower-alkynyl, lower-alkylene, aryl, or aryl-lower alkyl in a pharmaceutically acceptable carrier comprising a cellulose derivative.

15 Claims, No Drawings

COMPOSITIONS OF IODOBENZOIC ACID DERIVATIVES AND CELLULOSE DERIVATIVES FOR VISUALIZATION OF THE GASTROINTESTINAL TRACT

This application is a continuation in part of application Ser. No. 08/029,756 filed on Mar. 11, 1993 U.S. Pat. No. 5,312,616.

BACKGROUND OF THE INVENTION

1. Field of the Invention

This invention relates to x-ray contrast compositions containing the contrast agents iodobenzoic acid derivatives in combination with cellulose derivatives and methods for their use in diagnostic radiology of the gastrointestinal tract.

2. Reported Developments

Roentgenographic examination utilizing x-rays and computed tomography (hereinafter CT) scans of fractures and other conditions associated with the skeletal system is routinely practiced without the use of contrast agents. x-ray visualization of organs containing soft tissue, such as the gastrointestinal (hereinafter GI) tract, requires the use of contrast agents which attenuate x-ray radiation. D. P. Swanson et al in "Pharmaceuticals In Medical Imaging", 1990, MacMillan Publishing Company, provides an excellent background in medical imaging utilizing contrast agents and compositions therewith.

Roentgenographic examination of the GI tract are indicated for conditions of digestive disorders, changes in bowel habit, abdominal pain, GI bleeding and the like. Prior to radiological examination, administration of a radiopaque contrast medium is necessary to permit adequate delineation of the respective lumen or mucosal surface from surrounding soft tissues. Accordingly, a contrast medium is administered orally to visualize the mouth, pharynx, esophagus, stomach, duodenum and proximal small intestine. The contrast medium is administered rectally for examination of the distal small intestine and the colon.

The most widely used contrast agent for the visualization of the GI tract is barium sulfate administered as a suspension orally or rectally as an enema. (See, for example, U.S. Pat. Nos.: 2,659,690; 2,680,089; 3,216,900; 3,235,462; 4,038,379 and 4,120,946) Notwithstanding its relatively good contrast characteristics, negligible absorption from the GI tract following oral or rectal administration and speedy excretion from the body, barium sulfate has certain disadvantages. In the presence of intestinal fluids it lacks homogeneity and poorly adheres to mucus membranes which can result in poor x-ray images. In the colon, when administered as an enema, it flocculates and forms irregular clumps with fecal matter.

Iodinated organic compounds have also been used as GI contrast agents since the iodine atom is an effective x-ray absorber. They have the most versatility and are utilized in the widest variety of procedures. They are very absorptive of x-rays with which the iodine interacts and produce a so-called photoelectric effect which is a large magnification in contrast caused by the photons stopped in the iodine-containing medium. The magnification of contrast exceeds the level that would be expected from relative changes in density. Because of this magnification, relatively low concentrations of the contrast agent can be utilized. (For iodinated agents see, for example, U.S. Pat. Nos.: 2,786,055; 3,795,698; 2,820,814; 3,360,436; 3,574,718, 3,733,397; 4,735,795 and 5,047,228.)

The desiderata for an ideal GI contrast agent includes: good toxicological profile; the ability to fill the entire bowel/lumen and evenly coat the gut mucosa so that the presence of the bowel is detectable when the lumen is not distended; and nonirritation to the intestinal mucosa; and passage through the GI tract without producing artifacts or stimulating vigorous intestinal peristalsis.

These requirements were addressed by many investigators and their efforts resulted in great improvements over the years. The requirement of evenly coating the gut mucosa with a contrast agent to effectively cover the walls of the intestines proved to be rather difficult. Without meeting these requirements it is impossible to obtain x-ray pictures of high precision. To that end, the use of certain polymer additives were proposed as illustrated hereunder.

U.S. Pat. No. 4,069,306 discloses an x-ray contrast preparation which is said to adhere to the walls of body cavities. The preparation comprises a finely divided water-insoluble inorganic x-ray contrast agent and minute particles of a hydrophilic polymer which is insoluble in water but is water-swellable. The body cavity is supplied with such preparation suspended in water. The x-ray contrast agent is present in admixture with and/or enclosed in and/or adhered to said minute polymer particles.

U.S. Pat. No. 4,120,946 discloses a pharmaceutical composition for barium opacification of the digestive tract, comprising colloidal barium sulfate and a polyacrylamide in an aqueous vehicle. The polyacrylamide forms a viscous solution at low concentration which makes it possible to maintain the barium sulfate in suspension and at the same time permit good adherence of the preparation to the walls of the organ which it is desired to x-ray.

U.S. Pat. No. 5,019,370 discloses a biodegradable radiographic contrast medium comprising biodegradable polymeric spheres which carry a radiographically opaque element, such as iodine, bromine, samarium and erbium. The contrast medium is provided either in a dry or liquid state and may be administered intravenously, orally and intra-arterially.

While these polymeric materials greatly enhance attachment of the contrast agent used therewith to the walls of organs for better visualization thereof, they do not provide a uniform coating thereon. As such, there is still a need for an improved x-ray imaging medium that uniformly coats the soft tissues subjected to diagnostic x-ray examination.

We have now discovered that certain iodobenzoic acid derivatives in a pharmaceutically acceptable vehicle comprising a cellulose derivative provides excellent x-ray imaging medium.

SUMMARY OF THE INVENTION

It is the object of the present invention to provide compositions for coating the gastrointestinal tract of mammals to form an effective radiopaque coating thereon by which diagnostic examination of the GI tract may be accomplished.

The object of the present invention is achieved by a composition comprising: an iodobenzoic acid derivative as x-ray contrast agent in a pharmaceutically acceptable vehicle comprising a cellulose derivative.

In accordance with the invention there is further provided a method for x-ray diagnostic imaging of the GI tract which comprises orally or rectally administering to the patient an effective contrast producing amount of the above-described x-ray contrast compositions.

The x-ray contrast agent of the present invention is of the formula:

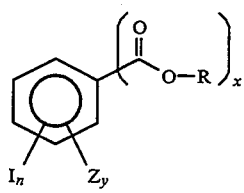

wherein

Z is H, halo, $C_1$–$C_{20}$ alkyl, cycloalkyl, lower alkoxy, cyano, where the alkyl and cycloalkyl groups can be substituted with halogen or halo-lower-alkyl groups;

R is $C_1$–$C_{25}$ alkyl, cycloalkyl, or halo-lower-alkyl, each of which may be optionally substituted with halo, fluoro-lower-alkyl, aryl, lower-alkoxy, hydroxy, carboxy, lower-alkoxy carbonyl or lower alkoxy-carbonyloxy; or $(CR_1R_2)_p$—$(CR_3=CR_4)_m Q$, or $(CR_1R_2)_p$—C≡C—Q;

$R_1$, $R_2$, $R_3$ and $R_4$ are independently lower-alkyl, optionally substituted with halo;

x is 1—3
y is 1—4;
n is 1—5;
m is 1—15;
p is 1—10; and

Q is H, lower-alkyl, lower-alkenyl, lower-alkynyl, lower-alkylene, aryl, or aryl-lower alkyl.

As used herein, the term halogen (or halo) means fluorine, chlorine, bromine or iodine.

As used herein, the term cycloalkyl means carbocyclic rings having from three to eight ring carbon atoms including cyclopropyl, cyclobutyl, cyclopentyl, cyclohexyl and cyclooctyl which may be substituted on any ring carbon atom thereof by one or more lower-alkyl groups, lower-alkoxy groups or halogens.

As used herein the terms lower-alkyl and lower-alkoxy mean monovalent aliphatic radicals, including branched chain radicals, of from one to ten carbon atoms. Thus, the lower-alkyl moiety of such groups include, for example, methyl, ethyl, propyl, isopropyl, n-butyl, sec-butyl, t-butyl, n-pentyl, 2-methyl-3-butyl, 1-methylbutyl, 2-methylbutyl, neopentyl, n-hexyl, 1-methylpentyl, 3-methylpentyl, 1-ethylbutyl, 2-ethylbutyl, 2-hexyl, 3-hexyl, 1,1,3,3-tetramethylpentyl, 1,1-dimethyloctyl and the like.

As used herein, the term lower-alkenyl and lower-alkynyl means monovalent, unsaturated radicals including branched chain radicals of from three to ten carbon atoms and thus include 1-ethenyl, 1-(2-propenyl), 1-(2-butenyl), 1-(1-methyl-2-propenyl), 1-(4-methyl-2-pentenyl), 4,4,6-trimethyl-2-heptenyl, 1-ethynyl, 1-(2-propynyl), 1-(2-butynyl), 1-(1-methyl-2-propynyl), 1-(4-methyl-2-pentynyl) and the like.

As used herein, the term alkylene means divalent saturated radicals, including branched chain radicals of from two to ten carbon atoms having their free valences on different carbon atoms and thus includes 1,2-ethylene, 1,3-propylene, 1,4-butylene, 1-methyl-1,2-ethylene, 1,8-octylene and the like.

As used herein, the term aryl means an aromatic hydrocarbon radical having six to ten carbon atoms. The preferred aryl groups are phenyl, substituted phenyl and naphthyl substituted by from one to three, the same or different members of the group consisting of lower-alkyl, halogen, hydroxy-lower-alkyl, alkoxy-lower-alkyl and hydroxy.

The x-ray contrast compound can comprise one, two, three or more iodine atoms per molecule; preferred species contain at least two, and more preferably, at least three iodine atoms per molecule.

The solid x-ray contrast agents in particulate forms useful in the practice of the present invention can be prepared by techniques known in the art. The solid agents are comminuted to the desired size using conventional milling methods, such as airjet or fragmentation milling. We have found that an effective average particle size of less than about 100 μ provides for good distribution and coating in the GI tract. As used herein, particle size refers to a number average particle size as measured by conventional techniques, such as sedimentation field flow fractionation and disk centrifugation. An effective average particle size of less than about 100 μ means that at least about 90% of the particles have a weight average particle size of less than about 100 μ as measured by art recognized techniques.

The cellulose derivative utilized in the present invention includes methylcellulose, carboxymethylcellulose, sodium carboxymethylcellulose, hydroxyethyl methylcellulose, hydroxypropyl methylcellulose; and microcrystalline cellulose having an average particle size of from 0.01 to 100 μ, more preferably of from 0.05 to 10 μ, and most preferably of 0.1 to 1μ.

The contrast agent and the cellulose derivative are formulated for administration using physiologically acceptable carriers or excipients in a manner within the skill of the art. The contrast agent and the cellulose derivative with the addition of pharmaceutically acceptable aids (such as surfactants and emulsifiers) and excipients are suspended or partially dissolved in an aqueous medium resulting in a dispersion, solution, suspension or emulsion.

A method for diagnostic imaging of the GI tract for use in medical procedures in accordance with this invention comprises orally or rectally administering to the mammalian patient in need of x-ray examination, an effective contrast producing amount of a composition of the present invention. After administration, at least a portion of the GI tract containing the administered composition is exposed to x-rays to produce an x-ray image pattern corresponding to the presence of the contrast agent, then the x-ray image is visualized and interpreted using techniques known in the art.

DETAILED DESCRIPTION OF THE INVENTION

Compounds of the present invention can be made according to the schematic procedure shown or other methods using commercially available starting materials, intermediates and reagents. Starting materials, reagents and solvents can be obtained from chemical suppliers such as Aldrich, Baker and Eastman Chemical Companies, or they may be prepared by techniques known in the art.

Scheme 1

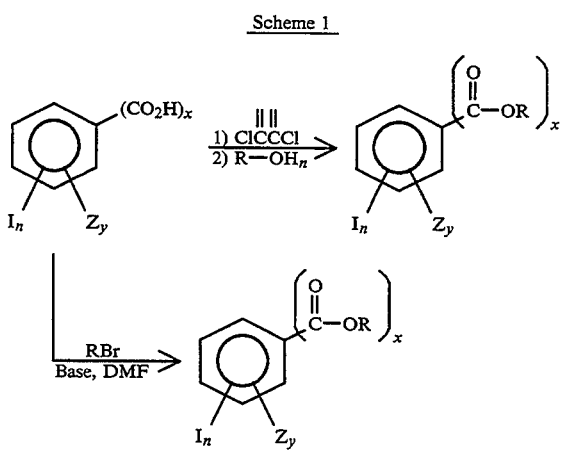

wherein x, y, n, Z and R are as above defined.

The following examples will further illustrate the compounds used in the present invention.

EXAMPLE 1

2-Octyl 2,3,5-triiodobenzoate

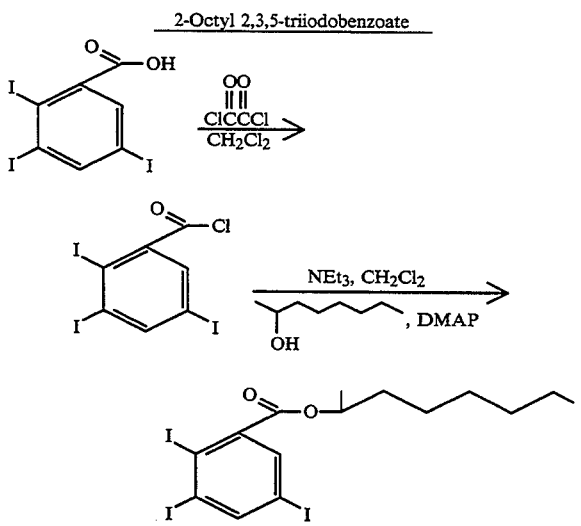

A mixture of 15.0 g (30.0 mmol) of 2,3,5-triiodobenzoic acid and 19.0 g (150 mmol) of oxalyl chloride in 60 ml of dry dichloromethane was placed under nitrogen and cooled to 0° C. Two drops of dry DMF were added, the ice bath was removed and the resulting suspension was stirred at room temperature for 1.5 hrs. The resulting brown solution was concentrated in vacuo to produce a tan solid. The solid was dissolved in 30 ml of dry toluene and was concentrated in vacuo. The toluene concentration was repeated two more times to yield 2,3,5-triiodobenzoyl chloride as a tan solid.

The 2,3,5-triiodobenzoyl chloride was dissolved in 60 ml of dry dichloromethane. The solution was cooled to 0° C. and 6.07 g (60.0 mmol) of triethylamine was added. The brown solution was placed under nitrogen and 4.30 g (33.0 mmol) of 2-octanol was added in 10 ml of dry dichloromethane. Dimethylaminopyridine (0.367 g, 3.00 mmol) was added and the resulting solution was stirred at room temperature for 72 hrs. The brown solution was partitioned between 100 ml of dichloromethane and 100 ml of 1M HCl. The dichloromethane layer was washed with saturated NaHCO$_3$ solution (50 ml) and brine (50 ml). The solution was dried over Na$_2$SO$_4$ and concentrated in vacuo to yield a dark brown oil (17.43 g). The oil was purified by flash chromatography using 436 g of silica gel and 5% ethyl acetate/hexane as the eluent. The first 600 ml to elute contained nothing while the pure product eluted with the next 700 ml. Concentration in vacuo afforded 15.68 g (85%) of the product as a yellow tinted oil.

Title Compound: $^1$H-NMR (300 MHz) and $^{13}$C (75 MHz) NMR Spectra were consistent with the desired structure. FAB/MS: (M+1)$^+$613. Calculated for C$_{15}$H$_{19}$I$_3$O$_2$: C, 29.44; H, 3.13. Found: C, 29.65; H, 3.03.

EXAMPLE 2

3,3,4,4,5,5,6,6,7,7,8,8-Dodecafluoro-2-octyl 2,3,5-triiodobenzoate

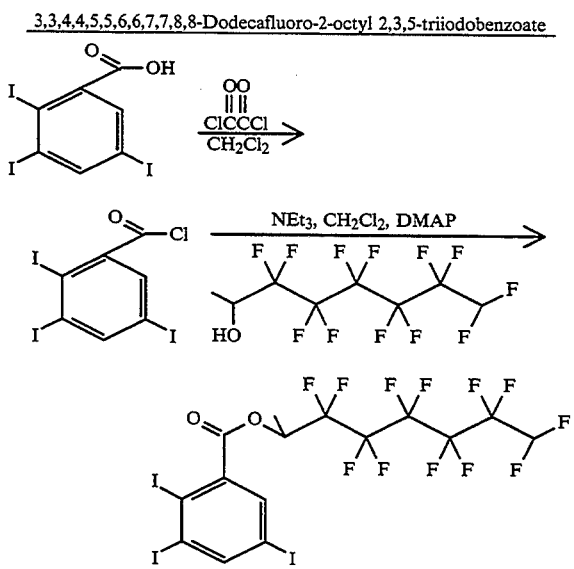

Using the same procedure as for 2-octyl-2,3,5-triiodobenzoate, 2,3,5-triiodobenzoyl chloride was prepared from 2.00 g of 2,3,5,-triiodobenzoic acid and 2.54 g of oxalyl chloride in dry dichloromethane. The 2,3,5-triiodobenzoyl chloride was dissolved in 8 ml of dry dichloromethane. The solution was cooled to 0° C. and 0.810 g (8.00 mmol) of triethylamine was added. The brown solution was placed under nitrogen before 1.52 g (4.40 mmol) of 3,3,4,4,5,5,6,6,7,7,8,8-dodecafluoro-2-octanol was added dropwise. Dimethylaminopyridine (0.049 g, 0.400 mmol) was added and the resulting solution was stirred at room temperature for 18 hrs. The brown solution was then partitioned between 100 ml of dichloromethane and 50 ml of 1M HCl. The dichloromethane layer was washed with saturated NaHCO$_3$ solution (50 ml) and brine (25 ml). The solution was dried over Na$_2$SO$_4$ and concentrated in vacuo to yield 3.11 g of a brown oil. The oil was purified by flash chromatography using 125 g of silica gel and 4% ethyl acetate/hexane as the eluent. The first 475 ml to elute contained nothing, while the pure product eluted with the next 200 ml. Concentration in vacuo afforded 2.36 g (71%) of the product as a colorless oil which slowly solidified to a white, waxy solid. Mp. 32°–35° C.

Title Compound: $^1$H-NMR (300 MHz) and $^{13}$C (75 MHz) NMR Spectra were consistent with the desired structure. Calculated for C$_{15}$H$_7$F$_{12}$I$_3$O$_2$: C, 21.76; H, 0.85; I, 45.98. Found: C, 21.86; H, 0.98; I, 46.25.

EXAMPLE 3

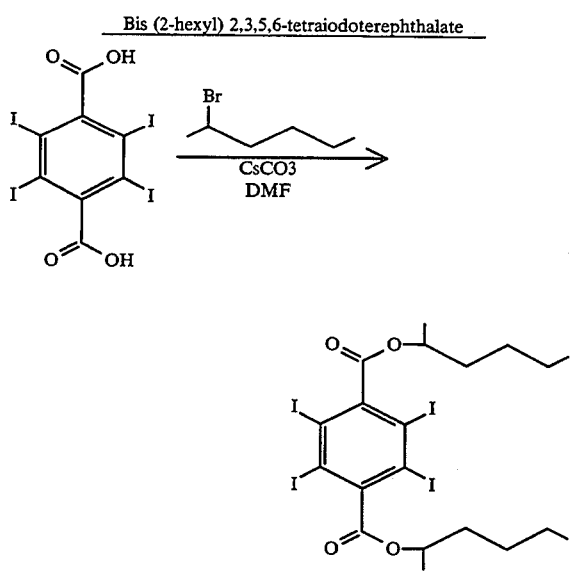

Cesium carbonate (1.63 g, 5.0 mmol) and 2-bromohexane (2.0 ml, 16 mmol) were added to a flask containing a stirred mixture of 2,3,5,6-tetraiodoterephthalate acid (1.4 g, 2.0 mmol) and dry DMF (20 ml). The reaction flask was immersed in an oil bath which was warmed to 76° C. over a period of 0.5 hr. After stirring under an atmosphere of $N_2$ for 22 hrs, the reaction was allowed to cool, diluted with DMF, filtered through a pad of celite and evaporated in vacuo. The resulting residue was taken up into EtOAc (200 ml), washed with saturated aqueous sodium bicarbonate (2×50 ml), water (50 ml) and brine (50 ml), dried ($Na_2SO_4$), filtered and evaporated in vacuo. Flash column chromatography (silica, 1:19; $Et_2O$:hexanes) provided bis (2-hexyl) 2,3,5,6-tetraiodoterephthalate (0.52 g, 44%) as a light yellow solid. Mp 114°–115° C.

Title Compound: $^1$H-NMR (300 MHz) and 13C (75 MHz) NMR Spectra were consistent with the desired structure. FAB/MS: M+838.

EXAMPLE 4

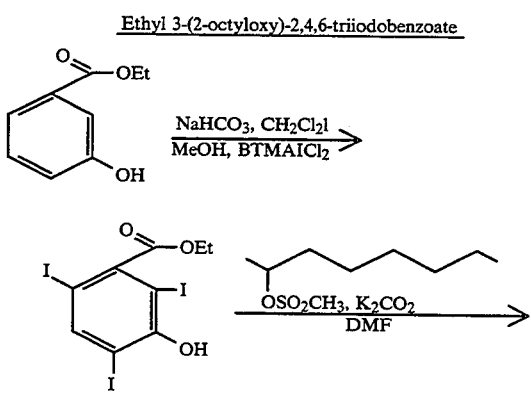

A mixture of 5.00 g (30.1 mmoles) of ethyl 3-hydroxybenzoate, 17.0 g (203 mmoles) of $NaHCO_3$ and 32.5 g (93.3 mmoles) of benzyltrimethylammonium dichloroiodate ($BTMAICl_2$) in 43.6 ml dichloromethane/16.6 ml methanol was placed under nitrogen and stirred for 22 hrs. The mixture was filtered and the $NaHCO_3$ was washed with 200 ml of dichloromethane. The flitrate was washed with 1M HCl (100 ml), 5% $NaHSO_3$ (100 ml) and brine (50 ml). The solution was dried over $Na_2SO_4$ and concentrated in vacuo to a tan oil which partially solidified overnight. The oily solid was purified by flash chromatography using 480 g of silica gel and 50% dichloromethane/1% methanol/49% hexane as the eluent. Concentration in vacuo afforded 12.41 g (76%) of ethyl 2,4,6- triiodo-3-hydroxybenzoate as a white solid. $^1$HNMR (300 MHZ) spectral data was consistent with desired structure.

A mixture of 5.41 g (25.7 mmoles) of 2-octylmethanesulfonate, 10.0 g (18.4 mmoles) of ethyl 2,4,6-triiodo-3-hydroxybenzoate and 5.08 g (36.8 mmoles) of potassium carbonate in 36 ml of dry DMF was stirred and heated to 72° C. under nitrogen for 17 hrs. The mixture was cooled and partitioned between 200 ml of ethyl acetate and 150 ml of 1M HCl. The ethyl acetate layer was then washed with water (200 ml) and brine (50 ml). The orange solution was dried over $Na_2SO_4$ and concentrated in vacuo to yield a orange oil (13.04 g). The oil was purified by flash chromatography using 390 g of silica gel with 5% ethyl acetate/hexane as eluent. Concentration in vacuo afforded 11.4 g (94%) of the product as a colorless oil.

Title Compound: $^1$H-NMR (300 MHz) and $^{13}$C (75 MHz) NMR Spectra were consistent with the desired structure. FAB/MS: (M+1)+657. Calculated for: $C_{17}H_{23}I_3O_3$: C, 31.12; H, 3.53; I, 58.03. Found: C, 31.41; H, 3.58; I, 57.97.

EXAMPLE 5

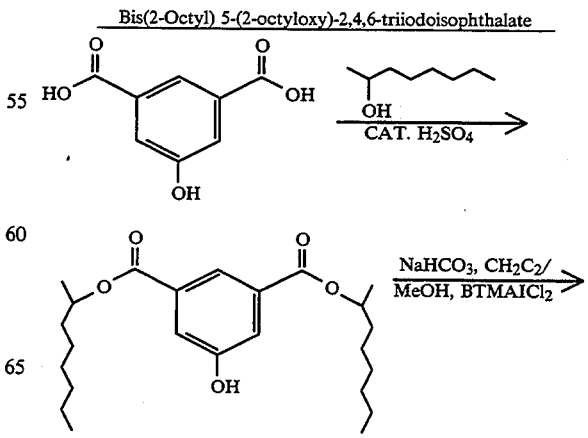

-continued

Bis(2-Octyl) 5-(2-octyloxy)-2,4,6-triiodoisophthalate

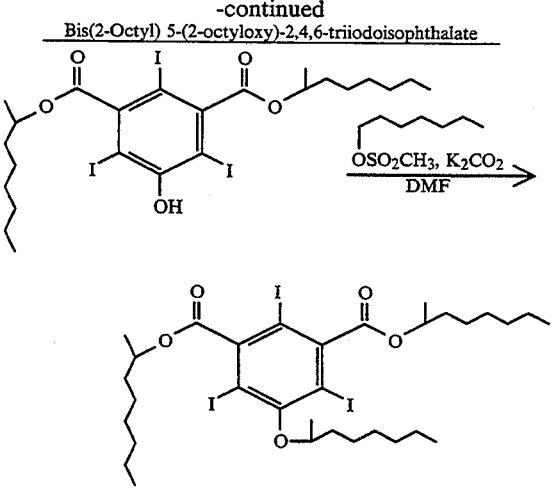

A mixture of 10.0 g (54.9 mmoles) of 5-hydroxyisophthalic acid, 57.2 g (439 mmoles) of 2-octanol and 0.31 ml (5.49 mmoles) of concentrated $H_2SO_4$ was left open and heated to 140° C. for 3.5 hrs. The mixture was cooled and partitioned between 200 ml of ethyl acetate and 100 ml of saturated $NaHCO_3$. The ethyl acetate layer was then washed with 50 ml of 1M HCl and brine (50 ml). The brown solution was dried over anhydrous $Na_2SO_4$ and concentrated in vacuo to yield a brown oil. The oil was distilled under high vacuum to remove the remaining 2-octanol. The oil which remained in the pot at 145° C. was cooled and purified by flash chromatography using 650 g of silica gel with 15% ethyl acetate/hexane as eluent. Concentration in vacuo afforded 18.15g (86%) of 2-octyl-5-hydroxy isophthalate as a yellow tinted oil. $^1H$ NMR (300 MHz) spectral data was consistent with the desired structure. The di-2-octyl-5-hydroxy isophthalate was iodinated and O-alkylated using the same procedure that was used to prepare WIN 68510. The product was obtained as a colorless oil (17.64 g, 67%).

Title Compound: $^1H$ NMR (300 MHz) and $^{13}C$ (75 MHz) NMR Spectra were consistent with the desired structure. FAB/MS: $(M-1)+895$. Calculated for $C_{32}H_{51}I_3O_5$: C, 42.87: H, 5.73: I, 42.47. Found: C, 43.32; H, 5.81; I, 42.35.

Compositions of the Present Invention

The contrast agents may be formulated for administration using physiologically acceptable carriers or excipients in a manner within the skill of the art. The compounds with the addition of pharmaceutically acceptable aids (such as surfactants and emulsifiers) and excipients may be suspended or partially dissolved in an aqueous medium resulting in a dispersion, solution or suspension. However, the oily contrast agents are preferably made into emulsions.

Compositions of the present invention comprise the following pharmaceutically acceptable components based on % w/v:

| Ingredients | Broad Range | More Preferred Range | Most Preferred Range |
| --- | --- | --- | --- |
| Contrast agent (mg I/ml of total suspension) | 30-200 | 40-160 | 85-120 |
| Cellulose derivative (% w/v) | 0.05-10 | 0.1-4 | 0.2-1 |

-continued

| Ingredients | Broad Range | More Preferred Range | Most Preferred Range |
| --- | --- | --- | --- |
| Oily Vehicle (% w/v) | 0.0-55 | 0.1-25 | 7-15 |
| Surfactant (% w/v) | 0.0-20 | 0.1-10 | 3-7 |
| Viscosity modifying excipients (% w/v) | 0.0-15 | 0.001-4 | 0.05-1 |
| Water - q.s. to 100% by volume | | | |

When the composition is used for CT imaging of the GI tract, the concentration of the x-ray contrast agent should be in the range of from 0.01 to 40 mg I/ml, more preferably of from 0.25 to 25 mg I/ml, and most preferably of from 4-12 mg I/ml.

The preferred cellulose derivative utilized in the present invention is AVICEL ® RC-591, which is a mixture of about 89 parts microcrystalline cellulose and about 11 parts of sodium carboxymethylcellulose.

In further reference to the components used in the compositions of the present invention the following should be noted.

The x-ray contrast agent present in concentrations lower than the above-stated minimum in formulations does not provide good quality x-ray or CT images, while concentrations above the maximum concentration render the GI tract too radiopaque and do not allow sufficient delineation of the GI tract.

In practicing the present invention an oil-in-water emulsion is preferred over a water-in-oil emulsion, suspension and dispersion. Oily materials, the density of which approximate the density of the aqueous phase impart stability to emulsions. For that reason, low density oils, such as mineral oils, are desirable in preparing the emulsions. When the x-ray contrast agents are oily substances at room temperature, the presence of an additional oily vehicle is not always necessary. Above about 55% w/v of oil the emulsion is no longer an oil-in-water emulsion but shifts to a water-in-oil emulsion.

Compositions without the presence of surfactants still provide excellent x-ray images, however, without surfactants the compositions are very difficult to emulsify and only suspensions/dispersions are produced which are less desirable for coating the GI tract and are also less stable on shelf-life. For reason of toxicity it is desirable to keep the concentration of certain surfactants as low as possible; above about 20% w/v the risk of oxicity rapidly increases.

While the iodobenzoic acid derivatives of the present invention in formulations with a pharmaceutically acceptable vehicle provide good quality x-ray images, the addition of a cellulose derivative to the formulations greatly increases the quality of the x-ray images. At the low extreme of the concentration range there is little or no benefit gained, while above the higher extreme of the concentration range the emulsion is too viscous for administration.

Depending on the form and amount of cellulose derivative used, additions of viscosity modifying agents may not be necessary; at higher levels than about 15% w/v the viscosity is too high and gels will tend to form.

The following formulation examples will further illustrate the invention.

EXAMPLE 6

| Components | Amounts in % w/v |
| --- | --- |
| 2-Octyl-2,3,5-triiodobenzoate | 17.50 |
| Light Mineral Oil, NF | 12.50 |
| Polysorbate 80 (Tween 80) | 3.37 |
| Sorbitan Mono-oleate (Span 80) | 1.64 |
| AVICEL ® RC-591 | 0.50 |
| q.s. with water to 100% by volume | |

EXAMPLE 7

| Components | Amounts in % w/v |
| --- | --- |
| 3,3,4,4,5,5,6,6,7,7,8,8-Dodecafluoro-2-octyl-2,3,5-triiodobenzoate | 25.00 |
| Polysorbate 80 (Tween 80) | 5.00 |
| AVICEL ® RC-591 | 6.50 |
| q.s. with water to 100% by volume | |

As known by those skilled in the art, surfactants or emulsifiers can reduce the interfacial tension between two immiscible phases, i.e., oil-in-aqueous medium. These agents can be used alone or in combination with other emulsifying agents and surfactants. For example, Dow Corning Medical Antifoam AF, which is a composition of 30% w/v polydimethylsiloxane simethicone and silica aerogel, 14% w/v stearate emulsifiers and 0.075% w/v sorbic acid, the balance being water, may be used by itself. Intralipid, which is an emulsion of fatty acids needs the presence of a suspending agent for it to form an acceptable emulsion with contrast agents of the present invention. The surface active agents may be cationic, anionic, nonionic, zwitterionic or a mixture of two or more of these agents.

Suitable cationic surfactants include cetyl trimethyl ammonium bromide. Suitable anionic agents include sodium lauryl sulphate, sodium heptadecyl sulphate, alkyl benzenesulphonic acids and salts thereof, sodium butylnapthalene sulfonate, and sulphosuccinates. Zwitterionic surface active agents are substances that when dissolved in water they behave as diprotic acids and, as they ionize, they behave both as a weak base and a weak acid. Since the two charges on the molecule balance each other out the molecules act as neutral molecules. The pH at which the zwitterion concentration is maximum is known as the isoelectric point. Compounds, such as certain amino acids having an isoelectric point at the desired pH of the formulations of the present invention are useful in practicing the present invention.

In preparing the formulations of the present invention we prefer to use nonionic emulsifiers or surface active agents which, similarly to the nonionic contrast agents, possess a superior toxicological profile to that of anionic, cationic or zwitterionic agents. In the nonionic emulsifying agents the proportions of hydrophilic and hydrophobic groups are about evenly balanced. They differ from anionic and cationic surfactants by the absence of charge on the molecule and, for that reason, are generally less of an irritant than the cationic or anionic surfactants. Nonionic surfactants include carboxylic esters, carboxylic amides, ethoxylated alkylphenols and ethoxylated aliphatic alcohols.

One particular type of carboxylic ester nonionic surface active agents are the partial, for example mono-, esters formed by the reaction of fatty and resin acids, for example of about 8 to about 18 carbon atoms, with polyhydric alcohols, for example glycerol, glycols such as mono-, di-, tetra- and hexaethylene glycol, sorbitan, and the like; and similar compounds formed by the direct addition of varying molar ratios of ethylene oxide to the hydroxy group of fatty acids.

Another type of carboxylic esters is the condensation products of fatty and resin partial acids, for example mono-, esters ethylene oxide, such as fatty or resin acid esters of polyoxyethylene sorbitan and sorbitol, for example polyoxyethylene sorbitan, monotall oil esters. These may contain, for example, from about 3 to about 80 oxyethylene units per molecule and fatty or resin acid groups of from about 8 to about 18 carbon atoms. Examples of naturally occurring fatty acid mixtures which may be used are those from coconut oil and tallow while examples of single fatty acids are dodecanoic acid and oleic acid.

Carboxylic amide nonionic surface active agents are the ammonia, monoethylamine and diethylamine amides of fatty acids having an acyl chain of from about 8 to about 18 carbon atoms.

The ethoxylated alkylphenol nonionic surface active agents include various polyethylene oxide condensates of alkylphenols, especially the condensation products of monoalkylphenols or dialkylphenols wherein the alkyl group contains about 6 to about 12 carbon atoms in either branched chain or particularly straight chain configuration, for example, octyl cresol, octyl phenol or nonyl phenol, with ethylene oxide, said ethylene oxide being present in amounts equal to from about 5 to about 25 moles of ethylene oxide per mole of alkylphenol.

Ethoxylated aliphatic alcohol nonionic surface active agents include the condensation products of aliphatic alcohols having from about 8 to 18 carbon atoms in either straight chain or branched chain configuration, for example oleyl or cetyl alcohol, with ethylene oxide, said ethylene oxide being present in equal amounts from about 30 to about 60 moles of ethylene oxide per mole of alcohol.

Preferred nonionic surface active agents include: sorbitan esters (sold under the trade name Span) having the formula:

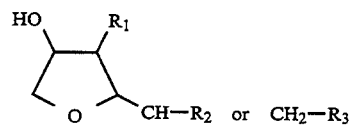

wherein
$R_1 = R_2 = $ OH, $R_3 = R$ for sorbitan monoesters, $R_1 = $ OH, $R_2 = R_3 = R$ for sorbitan diesters, $R_1 = R_2 = R_3 = R$ for sorbitan triesters, where $R = (C_{11}H_{23})$ COO for laurate, $(C_{17}H_{33})$ COO for oleate, $(C_{15}H_{31})$ COO for palmitate, $(C_{17}H_{35})$ COO for stearate.

Polyoxyethylene alkyl ethers (i.e. Brijs) having the formula:

$$CH_3(CH_2)_x(O-CH_2-CH_2)_yOH$$

where (x+1) is the number of carbon atoms in the alkyl chain, typically:

| 12 lauryl | (dodecyl) |
| --- | --- |
| 14 myristyl | (tetradecyl) |
| 16 cetyl | (hexadecyl) |

| -continued | |
|---|---|
| 18 stearyl | (octadecyl) | and y is the number of ethylene oxide groups in the hydrophilic chain, typically 10–60.

Polyoxyethylene sorbitan fatty acid esters (Polysorbates 20, 40, 60, 65, 80 & 85) sold under the trade names of Tweens, Crillers, Sorlares and Monitans, having the formulas (1) and (2)

Polyoxyethylene sorbitan monoester

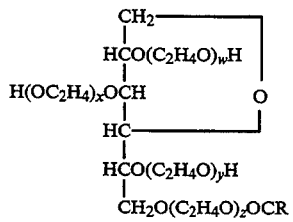   (1)

Polyoxyethylene sorbitan triester

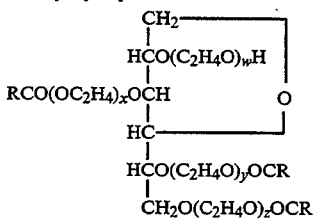   (2)

wherein

| | |
|---|---|
| w + x + y + z = 20 | (Polysorbate 20, 40, 60, 65, 80 and 85) |
| w + x + y + z = 5 | (Polysorbate 81) |
| w + x + y + z = 4 | (Polysorbate 21 and 61). |

Polyethylene stearates, such as:
poly(oxy-1,2-ethanediyl )$,\alpha$-hydro-$\omega$-hydroxyoctadecanoate; polyethylene glycol monostearate; and poly(oxy-1,2-ethanediyl)-$\alpha$-(1-oxooctadecyl)-$\omega$-hydroxy-polyethylene glycol monostearate.

The dosages of the contrast agent used according to the method of the present invention will vary according to the precise nature of the contrast agent used. Preferably, however, the dosage should be kept as low as is consistent with achieving contrast enhanced imaging. By employing as small amount of contrast agent as possible, toxicity potential is minimized. For most contrast agents of the present invention dosages will be in the range of from about 0.1 to about 16.0 g iodine/kg body weight, preferably in the range of from about 0.5 to about 6.0 g iodine/kg of body weight, and most preferably, in the range of from about 1.2 to about 2.0 g iodine/kg body weight for regular x-ray visualization of the GI tract. For CT scanning, the contrast agents of the present invention will be in the range of from about 1 to about 600 mg iodine/kg body weight, preferably in the range of from about 20 to about 200 mg iodine/kg body weight, and most preferably in the range of from about 40 to about 80 mg iodine/kg body weight.

The concentration of the contrast agent should be in the range of from about 0.001% w/v to about 75% w/v of the formulation, preferably from about 0.05% w/v to about 50% w/v, and most preferably of from about 0.1% w/v to about 20% w/v.

The invention having been fully described, it will be apparent to one skilled in the art that changes and modifications can be made thereto without departing from the spirit and scope thereof.

What is claimed is:

1. An x-ray contrast composition for oral or retrograde examination of the gastrointestinal tract comprising:
   (a) from about 0.01 to 200 mg of iodine per ml of the composition of an x-ray contrast producing agent having the formula, or pharmaceutically acceptable salt thereof

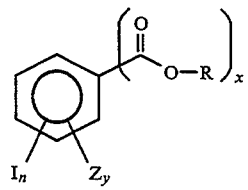

wherein

Z is H, halo, $C_1$–$C_{20}$ alkyl, cycloalkyl, lower alkoxy, cyano, where the alkyl and cycloalkyl groups can be substituted with halogen or halo-lower-alkyl groups;

R is $C_1$–$C_{25}$ alkyl, cycloalkyl, or halo-lower-alkyl, each of which may be optionally substituted with halo, fluoro-lower-alkyl, aryl, lower-alkoxy, hydroxy, carboxy, lower-alkoxy carbonyl or lower-alkoxy-carbonyloxy;

$(CR_1R_2)_p$- $(CR_3=CR_4)_m Q$, or $(CR_1R_2)_p$- C≡C - Q;

$R_1$, $R_2$, $R_3$ and $R_4$ are independently lower-alkyl, optionally substituted with halo;

x is 1—3 y is 1—4;

n is 1—5;

m is 1—15;

p is 1—10; and

Q is H, lower-alkyl, lower-alkenyl, lower-alkynyl, lower-alkylene, aryl, or aryl-lower alkyl;

(b) from 0.05 to 10% w/v of a cellulose derivative selected from the group consisting of methylcellulose, carboxymethylcellulose, sodium carboxymethylcellulose, hydroxyethyl methylcellulose, hydroxypropyl methylcellulose and microcrystalline cellulose;

(c) from 0 to 55% w/v of an oily vehicle;

(d) from 0 to 20% w/v of a surfactant selected from the group consisting of nonionic, anionic, cationic and zwitterionic surfactants;

(e) from 0 to 15% w/v of a viscosity modifying excipient; and (f) water to make 100% by volume.

2. The x-ray contrast composition according to claim 1 wherein said x-ray contrast agent is selected from the group consisting of: 2-octyl 2,3,5-triiodobenzoate, 3,3,4,4,5,5,6,6,7,7,8,8-dodecafluoro-2-octyl 2,3,5-triiodobenzoate and bis (2-hexyl) 2,3,5,6-tetraiodoterephthalate.

3. The x-ray contrast composition according to claim 1 wherein said x-ray contrast agent is selected from the group consisting of: ethyl 3- (2-octyloxy)-2,4,6-triiodo benzoate and bis(2-octyl) 5-(2-octyloxy)-2,4,6-triiodoisophthalate.

4. The x-ray contrast composition of claim 1 wherein said x-ray contrast producing agent is present in an amount of 30 to 200 mg of iodine per ml of the composition.

5. The x-ray contrast composition of claim 1 wherein said oily vehicle constitutes from 0.1 to 25% w/v of the composition.

6. The x-ray contrast composition of claim 1 wherein said surfactant constitutes from 0.1 to 10% of the composition.

7. The x-ray contrast composition of claim 1 wherein said microcrystalline cellulose has an average particle size of from 0.01 to 100 $\mu$.

8. The x-ray contrast composition of claim 7 wherein said microcrystalline cellulose is about 89 parts microcrystalline cellulose and about 11 parts of sodium carboxymethylcellulose.

9. The x-ray contrast composition of claim 1 wherein said nonionic surface active agent is selected from the group consisting of carboxylic esters, carboxylic amides, ethoxylated alklyphenols and ethoxylated aliphatic alcohols.

10. The x-ray contrast composition of claim 1 wherein said surfactant is sorbitan ester having the formula:

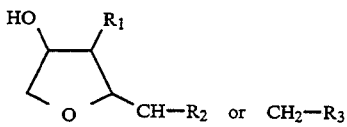

wherein $R_1=R_2=OH$, $R_3=R$ for sorbitan monoesters, $R_1=OH$, $R_2=R_3=R$ for sorbitan diesters, $R_1=R_2=R_3=R$ for sorbitan triesters, where $R=(C_{11}H_{23})$ COO for laurate, $(C_{17}H_{33})$ COO for oleate, $(C_{15}H_{31})$ COO for palmirate or $(C_{17}H_{35})$ COO for stearate.

11. The x-ray contrast composition of claim 1 wherein said surfactant is polyoxyethylene alkyl ether having the formula:

$CH_3(CH_2)_x(O-CH_2-CH_2)_yOH$ where (x+1) is the number of carbon atoms in the alkyl chain, and y is the number of ethylene oxide groups in the hydrophilic chain, from about 10 to about 60.

12. An x-ray contrast composition for oral or retrograde examination of the gastrointestinal tract comprising:

(a) from about 85 to 120 mg of iodine per ml of the composition of an x-ray contrast producing agent having the formula, or pharmaceutically acceptable salt thereof

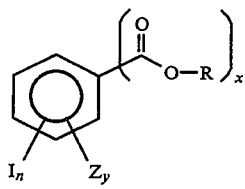

wherein

Z is H, halo, $C_1-C_{20}$ alkyl, cycloalkyl, lower alkoxy, cyano, where the alkyl and cycloalkyl groups can be substituted with halogen or halo-lower-alkyl groups;

R is $C_1-C_{25}$ alkyl, cycloalkyl, or halo-lower-alkyl, each of which may be optionally substituted with halo, fluoro-lower-alkyl, aryl, lower-alkoxy, hydroxy, carboxy, lower-alkoxy carbonyl or lower alkoxy-carbonyloxy;

$(CR_1R_2)_p$ - $(CR_3=CR_4)_mQ$, or $(CR_1R_2)_p$ - C≡C - Q;

$R_1$, $R_2$, $R_3$ and $R_4$ are independently lower-alkyl, optionally substituted with halo;

x is 1—3 y is 1—4;

n is 1—5;

m is 1—15;

p is 1—10; and

Q is H, lower-alkyl, lower-alkenyl, lower-alkynyl, lower-alkylene, aryl, or aryl-lower alkyl;

(b) from 0.2 to 1% w/v of a cellulose derivative selected from the group consisting of methylcellulose, carboxymethylcellulose, sodium carboxymethylcellulose, hydroxyethyl methylcellulose, hydroxypropyl methylcellulose and microcrystalline cellulose;

(c) from 7 to 15% w/v of a mineral oil;

(d) from 3 to 7% w/v of a surfactant selected from the group consisting of nonionic, anionic, cationic and zwitterionic surfactants;

(e) from 0.05 to 1% w/v of a viscosity modifying excipient; and (f) water to make 100% by volume.

13. The x-ray contrast composition of claim 12 wherein the average particle size of said microcrystalline cellulose is from 0.05 to 10 $\mu$.

14. The x-ray contrast composition of claim 12 wherein said composition is in the form of an oil-in-water emulsion.

15. A method of carrying out x-ray examination of the gastrointestinal tract of a patient, said method comprises the oral or rectal administration to the patient an x-ray contrast formulation comprising:

(a) from about 0.01 to 200 mg of iodine per ml of the composition of an x-ray contrast producing agent having the formula, or pharmaceutically acceptable salt thereof

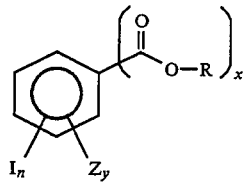

wherein

Z is H, halo, $C_1-C_{20}$ alkyl, cycloalkyl, lower alkoxy, cyano, where the alkyl and cycloalkyl groups can be substituted with halogen or halo-lower-alkyl groups;

R is $C_1-C_{25}$ alkyl, cycloalkyl, or halo-lower-alkyl, each of which may be optionally substituted with halo, fiuoro-lower-alkyl, aryl, lower-alkoxy, hydroxy, carboxy, lower-alkoxy carbonyl or lower-alkoxy-carbonyloxy;

$(CR_1R_2)_p$— $(CR_3=CR_4)_mQ$, or $(CR_1R_2)_p$ - C≡C - Q;

$R_1$, $R_2$, $R_3$ and $R_4$ are independently lower-alkyl, optionally substituted with halo;

x is 1—3 y is 1—4;
n is 1—5;
m is 1—15;
p is 1—10; and
Q is H, lower-alkyl, lower-alkenyl, lower-alkynyl, lower-alkylene, aryl, or aryl-lower alkyl;

(b) from 0.05 to 10% w/v of a cellulose derivative selected from the group consisting of methylcellulose, carboxymethylcellulose, sodium carboxymethylcellulose, hydroxyethyl methylcellulose, hydroxypropyl methylcellulose and microcrystalline cellulose;

(c) from 0 to 55% w/v of an oily vehicle;

(d) from 0 to 20% w/v of a surfactant selected from the group consisting of nonionic, anionic, cationic and zwitterionic surfactants;

(e) from 0 to 15% w/v of a viscosity modifying excipient; and (f) water to make 100% by volume.

* * * * *